(12) United States Patent
Luo et al.

(10) Patent No.: US 6,211,164 B1
(45) Date of Patent: Apr. 3, 2001

(54) ANTISENSE OLIGONUCLEOTIDES OF THE HUMAN CHK1 GENE AND USES THEREOF

(75) Inventors: Yan Luo, Lake Bluff; Vincent L. Giranda, Gurnee; Shayna K. Rockow-Magnone, Palatine, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/522,800

(22) Filed: Mar. 10, 2000

(51) Int. Cl.[7] .......................... C07H 21/02; C07H 21/04; A61K 31/70; A01N 43/04
(52) U.S. Cl. .............................. 514/44; 435/6; 435/91.1; 435/325; 435/375; 536/23.1; 536/24.31; 536/24.33; 536/24.5
(58) Field of Search .................. 536/23.1, 24.3, 536/24.31, 24.33, 24.5; 435/6, 91.1, 325, 375; 514/44

(56) References Cited

FOREIGN PATENT DOCUMENTS

WO99/11795 * 3/1999 (WO).

OTHER PUBLICATIONS

Paulovich et al., *Cell* 88:315–321 (1997).
Shieh et al., *Cell* 91:325–34 (1997).
Kastan et al., *Cancer Research* 51:6304–11 (1991).
el–Deiry et al., *Cancer Research* 54:1169–74 (1994).
Dulic et al., *Cell* 76:1013–1023 (1994).
King et al., *Cell* 79:563–71 (1994).
Lew et al., *Current Opinion in Cell Biology* 8:795–804 (1996).
Nurse et al., *Cell* 91:865–7 (1997).
Walworth et al., *Science* 271:353–6 (1996).
Furnari et al., *Science* 277:1495–7 (1997).
Furnari et al., *Molecular Biology of the Cell* 10:833–45 (1999).
Sanchez et al., *Science* 277:1497–501 (1997).
Peng et al., *Science* 277:1501–5 (1997).
Powell et al., *Cancer Research* 55:1643–8 (1995).
Yao et al., *Nature Medicine* 2:1140–3 (1996).
Andrea D. Branch, A good antisense molecule is hard to find, TIBS, 47–48, Feb. 1998.*
Stanley Crooke, Antisense Research and Applications, Chapter 1, Basic Principles of Antisense Therapeutics, Springer–Verlag Press, Berlin, Heidelberg, New York p. 3, Feb. 1998.*

* cited by examiner

*Primary Examiner*—Robert A. Schwartzman
*Assistant Examiner*—Janet L. Epps
(74) *Attorney, Agent, or Firm*—Cheryl L. Becker

(57) ABSTRACT

The subject invention relates to antisense oligonucleotides of the human Chk1 gene and to uses thereof. The human ChK1 gene is a major G2/M checkpoint gene that is activated in response to DNA damage. In particular, the gene transduces the inhibitory signal from DNA damage sensors to the basic cell cycle machinery. Thus, antisense oligonucleotides to the human Chk1 gene may be used, for example, to inhibit the gene thereby preventing G2 arrest induced by DNA damaging agents. Such antisense oligonucleotides should also further sensitize tumor cells thereby making them more sensitive to therapy than normal cells.

9 Claims, 12 Drawing Sheets

CHKLAS1:
5' UUACUCUAUUCACAGCAAG
CHKLAS2:
5' AGUUGAUGGAAGAAUCUCU
CHKLAS3:
5' GAGGUUAUCCCUUUCAUCC
CHKLAS4:
5' CAAGCCAAAGUCUGAGAUU
CHKLAS5:
5' UUCUCUUCUCUUCAGAAGU
CHKLAS6:
5' AUGAAAUUCUCUUCUCUUC
CHKLAS7:
5' CGAGCACCUCGGCGGACUG
CHKLAS8:
5' GCCAUGACUCCACCGAGCA
CHKLAS9:
5' GGCACUGCCAUGACUCCAC
CHKLAS10:
5' CACAAAGGGCACUGCCAUG
CHKLAS11:
5' CACCAAGUCCCAGUCUUCC
CHKLAS12:
5' GCACCUUCUCCCAGGGUUU
CHKLAS13:
5' UUUAAUAUCCCUGUGAGUU
CHKLAS14:
5' GGUUGGUCCCAUGGCAAUU

FIG.4

```
              10        20        30        40        50
      GGCCGGACAGTCCGCCGAGGTGCTCGGTGGAGTCATGGCAGTGCCCTTTG
      CCGGCCTGTCAGGCGGCTCCACGAGCCACCTCAGTACCGTCACGGGAAAC
                                        M   A   V   P   F>
                                      ___GENE=CHK1_____>

60        70        80        90        100
      TGGAAGACTGGGACTTGGTGCAAACCCTGGGAGAAGGTGCCTATGGAGAA
      ACCTTCTGACCCTGAACCACGTTTGGGACCCTCTTCCACGGATACCTCTT
        V   E   D   W   D   L   V   Q   T   L   G   E   G   A   Y   G   E>
      ___GENE=CHK1; SIMILAR TO S.POMBE CHK1 PROTEIN ___>

110       120       130       140       150
      GTTCAACTTGCTGTGAATAGAGTAACTGAAGAAGCAGTCGCAGTGAAGAT
      CAAGTTGAACGACACTTATCTCATTGACTTCTTCGTCAGCGTCACTTCTA
        V   Q   L   A   V   N   R   V   T   E   E   A   V   A   V   K   I>
      ___GENE=CHK1; SIMILAR TO S.POMBE CHK1 PROTEIN ___>

160       170       180       190       200
      TGTAGATATGAAGCGTGCCGTAGACTGTCCAGAAAATATTAAGAAAGAGA
      ACATCTATACTTCGCACGGCATCTGACAGGTCTTTTATAATTCTTTCTCT
        V   D   M   K   R   A   V   D   C   P   E   N   I   K   K   E>
      ___GENE=CHK1; SIMILAR TO S.POMBE CHK1 PROTEIN ___>

210       220       230       240       250
      TCTGTATCAATAAAATGCTAAATCATGAAAATGTAGTAAAATTCTATGGT
      AGACATAGTTATTTTACGATTTAGTACTTTTACATCATTTTAAGATACCA
        I   C   I   N   K   M   L   N   H   E   N   V   V   K   F   Y   G>
      ___GENE=CHK1; SIMILAR TO S.POMBE CHK1 PROTEIN ___>

260       270       280       290       300
      CACAGGAGAGAAGGCAATATCCAATATTTATTTCTGGAGTACTGTAGTGG
      GTGTCCTCTCTTCCGTTATAGGTTATAAATAAAGACCTCATGACATCACC
        H   R   R   E   G   N   I   Q   Y   L   F   L   E   Y   C   S   G>
      ___GENE=CHK1; SIMILAR TO S.POMBE CHK1 PROTEIN ___>

310       320       330       340       350
      AGGAGAGCTTTTTGACAGAATAGAGCCAGACATAGGCATGCCTGAACCAG
      TCCTCTCGAAAAACTGTCTTATCTCGGTCTGTATCCGTACGGACTTGGTC
         G   E   L   F   D   R   I   E   P   D   I   G   M   P   E   P>
      ___GENE=CHK1; SIMILAR TO S.POMBE CHK1 PROTEIN ___>
```

FIG.8A

```
            360       370       380       390       400
ATGCTCAGAGATTCTTCCATCAACTCATGGCAGGGGTGGTTTATCTGCAT
TACGAGTCTCTAAGAAGGTAGTTGAGTACCGTCCCCACCAAATAGACGTA
 D  A  Q  R  F  F  H  Q  L  M  A  G  V  V  Y  L  H>
___GENE=CHK1; SIMILAR TO S.POMBE CHK1 PROTEIN ___>

410       420       430       440       450
GGTATTGGAATATCTCACAGGGATATTAAACCAGAAAATCTCCTGTTGGA
CCATAACCTTATTGAGTGTCCCTATAATTTGGTCTTTTAGAAGACAACCT
  G  I  G  I  T  H  R  D  I  K  P  E  N  L  L  L  D>
___GENE=CHK1; SIMILAR TO S.POMBE CHK1 PROTEIN ___>

460       470       480       490       500
TGAAAGGGATAACCTCAAAATCTCAGACTTTGGCTTGGCAACAGTATTTC
ACTTTCCCTATTGGAGTTTTAGAGTCTGAAACCGAACCGTTGTCATAAAG
   E  R  D  N  L  K  I  S  D  F  G  L  A  T  V  F>
___GENE=CHK1; SIMILAR TO S.POMBE CHK1 PROTEIN ___>

510       520       530       540       550
GGTATAATAATCGTGAGCGTTTGTTGAACAAGATGTGTGGTACTTTACCA
CCATATTATTAGCACTCGCAAACAACTTGTTCTACACACCATGAAATGGT
  R  Y  N  N  R  E  R  L  L  N  K  M  C  G  T  L  P>
___GENE=CHK1; SIMILAR TO S.POMBE CHK1 PROTEIN ___>

560       570       580       590       600
TATGTTGCTCCAGAACTTCTGAAGAGAAGAGAATTTCATGCAGAACCAGT
ATACAACGAGGTCTTGAAGACTTCTCTTCTCTTAAAGTACGTCTTGGTCA
  Y  V  A  P  E  L  L  K  R  R  E  F  H  A  E  P  V>
___GENE=CHK1; SIMILAR TO S.POMBE CHK1 PROTEIN ___>

610       620       630       640       650
TGATGTTTGGTCCTGTGGAATAGTACTTACTGCAATGCTCGCTGGAGAAT
ACTACAAACCAGGACACCTTATCATGAATGACGTTACGAGCGACCTCTTA
   D  V  W  S  C  G  I  V  L  T  A  M  L  A  G  E>
___GENE=CHK1; SIMILAR TO S.POMBE CHK1 PROTEIN ___>

660       670       680       690       700
TGCCATGGGACCAACCCAGTGACAGCTGTCAGGAGTATTCTGACTGGAAA
ACGGTACCCTGGTTGGGTCACTGTCGACAGTCCTCATAAGACTGACCTTT
  L  P  W  D  Q  P  S  D  S  C  Q  E  Y  S  D  W  K>
___GENE=CHK1; SIMILAR TO S.POMBE CHK1 PROTEIN ___>
```

FIG.8B

```
                710       720       730       740       750
         GAAAAAAAAAACATACCTCAACCCTTGGAAAAAAATCGATTCTGCTCCTCT
         CTTTTTTTTTTGTATGGAGTTGGGAACCTTTTTTTAGCTAAGACGAGGAGA
           E  K  K  T  Y  L  N  P  W  K  K  I  D  S  A  P  L>
         ___GENE=CHK1; SIMILAR TO S.POMBE CHK1 PROTEIN   ___>

760       770       780       790       800
         AGCTCTGCTGCATAAAATCTTAGTTGAGAATCCATCAGCAAGAATTACCA
         TCGAGACGACGTATTTTAGAATCAACTCTTAGGTAGTCGTTCTTAATGGT
            A  L  L  H  K  I  L  V  E  N  P  S  A  R  I  T>
         ___GENE=CHKI; SIMILAR TO S.POMBE CHK1 PROTEIN   ___>

810       820       830       840       850
         TTCCAGACATCAAAAAAGATAGATGGTACAACAAACCCCTCAAGAAAGGG
         AAGGTCTGTAGTTTTTTCTATCTACCATGTTGTTTGGGGAGTTCTTTCCC
            I  P  D  I  K  K  D  R  W  Y  N  K  P  L  K  K  G>
         ___GENE=CHK1; SIMILAR TO S.POMBE CHK1 PROTEIN   ___>

860       870       880       890       900
         GCAAAAAGGCCCCGAGTCACTTCAGGTGGTGTGTCAGAGTCTCCCAGTGG
         CGTTTTTCCGGGGCTCAGTGAAGTCCACCACACAGTCTCAGAGGGTCACC
            A  K  R  P  R  V  T  S  G  G  V  S  E  S  P  S  G>
         ___GENE=CHK1; SIMILAR TO S.POMBE CHK1 PROTEIN   ___>

910       920       930       940       950
         ATTTTCTAAGCACATTCAATCCAATTTGGACTTCTCTCCAGTAAACAGTG
         TAAAAGATTCGTGTAAGTTAGGTTAAACCTGAAGAGAGGTCATTTGTCAC
            F  S  K  H  I  Q  S  N  L  D  F  S  P  V  N  S>
         ___GENE=CHK1; SIMILAR TO S.POMBE CHK1 PROTEIN   ___>

960       970       980       990       1000
         CTTCTAGTGAAGAAAATGTGAAGTACTCCAGTTCTCAGCCAGAACCCCGC
         GAAGATCACTTCTTTTACACTTCATGAGGTCAAGAGTCGGTCTTGGGGCG
            A  S  S  E  E  N  V  K  Y  S  S  S  Q  P  E  P  R>
         ___GENE=CHK1; SIMILAR TO S.POMBE CHK1 PROTEIN   ___>

1010      1020      1030      1040      1050
         ACAGGTCTTTCCTTATGGGATACCAGCCCCTCATACATTGATAAATTGGT
         TGTCCAGAAAGGAATACCCTATGGTCGGGGAGTATGTAACTATTTAACCA
            T  G  L  S  L  W  D  T  S  P  S  Y  I  D  K  L  V>
         ___GENE=CHK1; SIMILAR TO S.POMBE CHK1 PROTEIN   ___>
```

FIG.8C

```
              1060      1070      1080      1090      1100
     ACAAGGGATCAGCTTTTCCCAGCCCACATGTCCTGATCATATGCTTTTGA
     TGTTCCCTAGTCGAAAAGGGTCGGGTGTACAGGACTAGTATACGAAAACT
        Q  G  I  S  F  S  Q  P  T  C  P  D  H  M  L  L>
     ___GENE=CHK1; SIMILAR TO S.POMBE CHK1 PROTEIN ____>

1110      1120      1130      1140      1150
     ATAGTCAGTTACTTGGCACCCCAGGATCCTCACAGAACCCCTGGCAGCGG
     TATCAGTCAATGAACCGTGGGGTCCTAGGAGTGTCTTGGGGACCGTCGCC
        N  S  Q  L  L  G  T  P  G  S  S  Q  N  P  W  Q  R>
     ___GENE=CHK1; SIMILAR TO S.POMBE CHK1 PROTEIN ____>

1160      1170      1180      1190      1200
     TTGGTCAAAAGAATGACACGATTCTTTACCAAATTGGATGCAGACAAATC
     AACCAGTTTTCTTACTGTGCTAAGAAATGGTTTAACCTACGTCTGTTTAG
        L  V  K  R  M  T  R  F  F  T  K  L  D  A  D  K  S>
     ___GENE=CHK1; SIMILAR TO S.POMBE CHK1 PROTEIN ____>

1210      1220      1230      1240      1250
     TTATCAATGCCTGAAAGAGACTTGTGAGAAGTTGGGCTATCAATGGAAGA
     AATAGTTACGGACTTTCTCTGAACACTCTTCAACCCGATAGTTACCTTCT
        Y  Q  C  L  K  E  T  C  E  K  L  G  Y  Q  W  K>
     ___GENE=CHK1; SIMILAR TO S.POMBE CHK1 PROTEIN ____>

1260      1270      1280      1290      1300
     AAAGTTGTATGAATCAGGTTACTATATCAACAACTGATAGGAGAAACAAT
     TTTCAACATACTTAGTCCAATGATATAGTTGTTGACTATCCTCTTTGTTA
        K  S  C  M  N  Q  V  T  I  S  T  T  D  R  R  N  N>
     ___GENE=CHK1; SIMILAR TO S.POMBE CHK1 PROTEIN ____>

1310      1320      1330      1340      1350
     AAACTCATTTTCAAAGTGAATTTGTTAGAAATGGATGATAAAATATTGGT
     TTTGAGTAAAAGTTTCACTTAAACAATCTTTACCTACTATTTTATAACCA
        K  L  I  F  K  V  N  L  L  E  M  D  D  K  I  L  V>
     ___GENE=CHK1; SIMILAR TO S.POMBE CHK1 PROTEIN ____>

1360      1370      1380      1390      1400
     TGACTTCCGGCTTTCTAAGGGTGATGGATTGGAGTTCAAGAGACACTTCC
     ACTGAAGGCCGAAAGATTCCCACTACCTAACCTCAAGTTCTCTGTGAAGG
        D  F  R  L  S  K  G  D  G  L  E  F  K  R  H  F>
     ___GENE=CHK1; SIMILAR TO S.POMBE CHK1 PROTEIN ____>
```

FIG. 8D

```
                1410      1420      1430      1440      1450
            TGAAGATTAAAGGGAAGCTGATTGATATTGTGAGCAGCCAGAAGGTTTGG
            ACTTCTAATTTCCCTTCGACTAACTATAACACTCGTCGGTCTTCCAAACC
             L  K  I  K  G  K  L  I  D  I  V  S  S  Q  K  V  W>
             ___GENE=CHK1; SIMILAR TO S.POMBE CHK1 PROTEIN    >

1460      1470      1480      1490      1500
            CTTCCTGCCACATGATCGGACCATCGGCTCTGGGGAATCCTGGTGAATAT
            GAAGGACGGTGTACTAGCCTGGTAGCCGAGACCCCTTAGGACCACTTATA
             L  P  A  T  *>
             ___GENE=CHK___>

1510      1520      1530      1540      1550
            AGTGCTGCTATGTTGACATTATTCTTCCTAGAGAAGATTATCCTGTCCTG
            TCACGACGATACAACTGTAATAAGAAGGATCTCTTCTAATAGGACAGGAC 1560      1570      1580      1590      1600
            CAAACTGCAAATAGTAGTTCCTGAAGTGTTCACTTCCCTGTTTATCCAAA
            GTTTGACGTTTATCATCAAGGACTTCACAAGTGAAGGGACAAATAGGTTT 1610      1620      1630      1640      1650
            CATCTTCCAATTTATTTTGTTTGTTCGGCATACAAATAATACCTATATCT
            GTAGAAGGTTAAATAAAACAAACAAGCCGTATGTTTATTATGGATATAGA 1660      1670      1680      1690      1700
            TAATTGTAAGCAAAACTTTGGGGAAAGGATGAATAGAATTCATTTGATTA
            ATTAACATTCGTTTTGAAACCCCTTTCCTACTTATCTTAAGTAAACTAAT 1710      1720      1730      1740      1750
            TTTCTTCATGTGTGTTTAGTATCTGAATTTGAAACTCATCTGGTGGAAAC
            AAAGAAGTACACACAAATCATAGACTTAAACTTTGAGTAGACCACCTTTG 1760      1770      1780      1790      1800
            CAAGTTTCAGGGGACATGAGTTTTCCAGCTTTTATACACACGTATCTCAT
            GTTCAAAGTCCCCTGTACTCAAAAGGTCGAAAATATGTGTGCATAGAGTA 1810      1820
            TTTTATCAAAACATTTTGTTT
            AAAATAGTTTTGTAAAACAAA
```

ANTISENSE OLIGONUCLEOTIDES OF THE HUMAN CHK1 GENE AND USES THEREOF

BACKGROUND OF THE INVENTION

1. Technical Field

The subject invention relates to the construction of antisense oligonucleotides of the human Chk1 gene and to uses thereof. The human Chk1 gene is a major G2/M checkpoint gene that is activated in response to DNA damage. In particular, the gene transduces the inhibitory signal from DNA damage sensors to the basic cell cycle machinery. Thus, antisense oligonucleotides to the human Chk1 gene may be used to inhibit gene expression thereby preventing G2 arrest induced by DNA damaging agents. Additionally, antisense oligonucleotides may act to sensitize tumor cells thereby making them more sensitive to therapy than normal cells.

2. Background Information

Many cancer therapeutic reagents cause cell death by inducing severe cellular DNA damage. Such DNA damage elicits two responses in normal, eukaryotic cells: 1) cell cycle arrest and 2) DNA repair to maintain genetic fidelity. In particular, checkpoint genes are activated in response to DNA damage. The gene products of these checkpoint genes form signal transduction pathways that transduce inhibitory signals from the DNA damage sensors to the basic cell cycle machinery and result in cell cycle arrest at both the G1 and G2 phases. Simultaneously, DNA damage also induces activation of transcription and production enzymes that facilitate DNA repair (Paulovich et al., *Cell* 88:315–321 (1997))).

p53 is the major G1 phase checkpoint gene. This protein is activated in the event of DNA damage (Shieh et al., *Cell* 91:325–34 (1997); Kastan et al., *Cancer Research* 51:6304–11 (1991)). (It transcriptionally activates cell cycle inhibitors such as p21, which, in turn, inhibit G1 cyclin-Cdks, thereby preventing cells from traversing the G1/S boundary (el-Deiry et al., *Cancer Research* 54:1169–74 (1994); Dulic et al., *Cell* 76:1013–1023 (1994)).

At the G2/M boundary, the onset of mitosis depends on the active cyclin B-Cdc2 kinase complex (King et al., *Cell* 79:563–71 (1994); Lew et al., *Current Opinion in Cell Biology* 8:795–804 (1996)). Wee1 kinase and Cdc25C phosphatase regulate Cdc2 activity. In particular, Wee1 phosphorylates Cdc2 at tyrosine 15 which inactivates Cdc2. Cdc25C removes this inhibitory phosphate and keeps Cdc2 active (Nurse et al., *Cell* 91: 865–7 (1997)).

During the G2 phase, DNA damages leads to Chk1 phosphorylation and activation in an ATM dependent manner (Walworth et al., *Science* 271:353–6 (1996)). Active Chk1 phosphorylates Cdc25C at serine 216, and 14–3–3 proteins export the phosphorylated Cdc25c out of the nucleus of the cell. Thus, Cdc2 is inhibited by the phosphorylation at tyrosine 15, and cells are halted at G2 for DNA repair (Furnari et al., *Science* 277:1495–7 (1997); Furnari et al., *Molecular Biology of the Cell* 10:833–45 (1999); Sanchez et al., *Science* 277:1497–501 (1997); Peng et al., *Science* 277:1501–5 (1997)).

It has been known for some time that the majority of tumors have defects in G1 checkpoint machinery, many of them due to p53 mutations (Kastan et al. (1991) Cancer Research 51:6304–11). In the event of DNA damage, these G1 checkpoint-defective tumor cells depend primarily on the G2 checkpoint for DNA repair. The inability to repair DNA at the G1 checkpoint is consistent with the observation that tumor cells are more sensitive to DNA damaging therapeutics than are normal cells. Given this observation, the toxicity to normal tissues is still a common side effect in cancer therapy. Significant effort has therefore been expended to specifically sensitize tumors to cancer drugs or radiotherapy.

One such approach is to abrogate G2 arrest in response to DNA damage (Powell et al., *Cancer Research* 55: 1643–8 (1995); Yao et al., *Nature Medicine* 2:1140–3 (1996)). Since G1 checkpoint-defective tumor cells can only repair DNA in G2 phase, inhibition of the Chk1 gene is expected to abrogate the G2 arrest in DNA damage response and increase the sensitivity to chemotherapy/radiotherapy more profoundly in tumor cells than in normal cells.

All U.S. patents and publications are herein incorporated in their entirety by reference.

SUMMARY OF THE INVENTION

The subject invention encompasses an isolated antisense nucleotide sequence of a mammalian Chk1 gene which inhibits expression of Chk1 protein. This sequence may be represented by SEQ ID NO:1 (oligo 7), SEQ ID NO:2 (oligo 8), SEQ ID NO:3 (oligo 9), SEQ ID NO:4 (oligo 14), or a fragment thereof which specifically hybridizes to the complement of one of these sequences. The sequence may also have at least 40% identity to SEQ ID NO:1, SEQ ID NO:2, SEQ ID:3 or SEQ:4, or it may be a fragment thereof which hybridizes to the complement of the sequence having 40% identity to the sequence having at least 40% identity to SEQ ID NO:1, SEQ ID NO:2, SEQ ID NO:3 or SEQ ID NO:4.

Additionally, the present method includes a method of preventing expression of Chk1 protein by a cell comprising the step of introducing into the cell a vector comprising at least one of the above nucleotide sequences or fragments thereof.

Furthermore, the present invention also encompasses a method of preventing expression of Chk1 protein by a cell comprising the step of introducing into the cell a vector comprising an isolated nucleotide sequence having at least 40% identity to a nucleotide sequence selected from the group consisting of SEQ ID NO:1, SEQ ID NO:2, SEQ ID NO:3, SEQ ID NO:4, and a fragment thereof which specifically hybridizes to the complement of the isolated nucleotide sequence.

The present invention also includes a method of screening a compound for ability to inhibit expression of Chk1 protein by a cell comprising the steps of exposing the cell to the compound of interest and measuring expression of Chk1 protein by the cell, lack of expression of Chk1 protein indicating a compound having the ability to inhibit expression of Chk1 protein.

Additionally, the invention also encompasses a pharmaceutical composition comprising an isolated antisense nucleotide sequence of a mammalian Chk1 gene or homologue thereof which inhibits expression of a Chk1 protein and a pharmaceutically acceptable carrier.

The present invention also includes a pharmaceutical composition comprising: 1) an isolated nucleotide sequence having at least 40% identity to a nucleotide sequence selected from the group consisting of SEQ ID NO:1, SEQ ID NO:2, SEQ ID NO:3 and SEQ ID NO:4 or 2) a fragment thereof which specifically hybridizes to the complement of the isolated nucleotide sequence, and 3) a pharmaceutically acceptable carrier. More than one of the sequences and/or fragments thereof may be included in the composition.

Additionally, the present invention encompasses a method of sensitizing malignant cells to chemotherapy, in a patient in need of such treatment, comprising the step of administering to the patient an effective amount of the pharmaceutical composition or compositions described above.

BRIEF DESCRIPTION OF THE DRAWINGS

FIG. 4 represents the nucleotide sequences of the designed antisense Chk1 oligonucleotides (SEQ ID NO: 1–14).

FIG. 8 represents the complete DNA sequence (sense strand SEQ ID NO:15 and antisense strand SEQ ID NO:17) and peptide sequence (SEQ ID NO: 16) of the Chk1 gene.

DETAILED DESCRIPTION OF THE INVENTION

Figure 1:
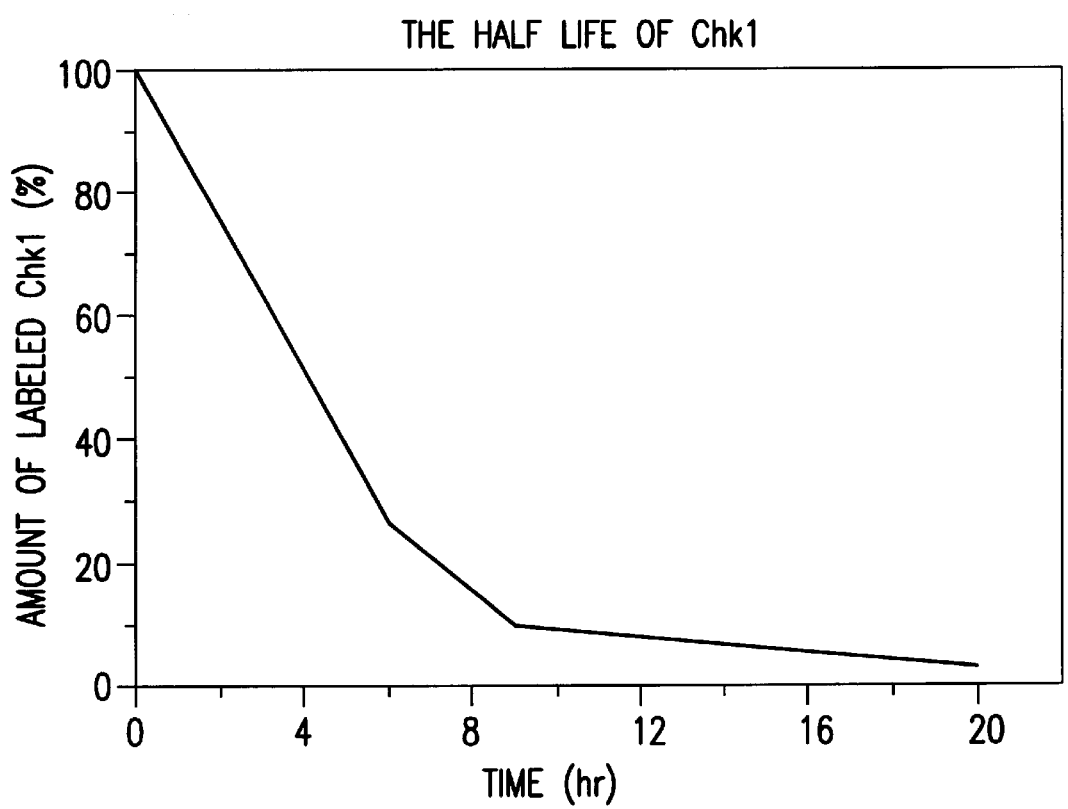
FIG. 1 illustrates the half-life of the Chk1 protein.

The subject invention relates to the design of novel antisense oligonucleotides of Chk1 that may be used for several purposes including, for example, therapeutic purposes. In particular, such oligonucleotides may be used to inhibit expression of the Chk1 protein, thereby enhancing specific defects in tumor cells and making those cells more sensitive to radiation or chemotherapy, as compared to normal cells.

The Antisense Oligonucleotides of Chk1

The nucleotide sequences of the designed antisense oligonucleotides of the Chk1 gene are shown in FIG. 4. The present invention encompasses these sequences, fragments thereof, complements of the sequences and fragments, as well as sequences corresponding to (i.e., having identity to) or complementary to at least about 40%, preferably at least about 50%, and more preferably at least about 70% of the nucleotides in FIG. 4. Furthermore, the present invention also includes fragments and complements of these sequences as well.

For purposes of the present invention, a "fragment" is of a nucleotide sequence is defined as a contiguous sequence of approximately at least 6, preferably at least about 8, more preferably at least about 10–12 nucleotides, and even more preferably at least about 15–18 nucleotides corresponding to a region of the specified nucleotide sequence.

Furthermore, for purposes of the present invention, a "complement" is defined as a sequence which pairs to a given sequence based upon base-pairing rules. For example, a sequence A-G-T in one nucleotide strand is "complementary" to T-C-A in the other strand.

Sequence identity or percent identity is the number of exact matches between two aligned sequences divided by the length of the shorter sequence and multiplied by 100. An approximate alignment for nucleic acid sequences is provided by the local homology algorithm of Smith and Waterman, *Advances in Applied Mathematics* 2:482–489 (1981). This algorithm may be extended to use with peptide or protein sequences using the scoring matrix created by Dayhoff, *Atlas of Protein Sequences and Structure*, M. O. Dayhoff ed., 5 Suppl. 3:353–358, National Biomedical Research Foundation, Washington, D.C., USA, and normalized by Gribskov, *Nucl. Acids Res.* 14(6):6745–66763 (1986). An implementation of this algorithm for nucleic acid and peptide sequences is provided by the Genetics Computer Group (Madison, Wis.) in the BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

Sequences related to the anti-sense oligonucleotides may be derived from non-human sources (e.g., bacterial, viral, mammalian, etc.) and are also covered by the present invention. Functional equivalents of the above-sequences (i.e., sequences having the ability to inhibit partial or complete expression of the Chk1 gene) and, in particular, sequences that have the ability to hybridize to the equivalent regions of Chk1 genes present in non-mammalian species, are also encompassed by the present invention. More specifically, such equivalents have the ability to hybridize to the Chk1 protein coding region of the Chk1 nucleotide sequence.

A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.). The conditions of temperature and ionic strength determine the "stringency" of the hybridization. "Hybridization" requires that two nucleic acid sequences contain complementary sequences. However, depending on the stringency of the hybridization, mismatches between bases may occur. The appropriate stringency for hybridizing nucleic acids depends on the length of the nucleic acids and the degree of complementation. Such variables are well known in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

Additionally, the present invention encompasses the purified polypeptides encoded by the translated amino acid sequences corresponding to the nucleotide sequences illustrated in FIG. 4. The invention also includes those peptides, polypeptides or proteins, or fragments thereof, having an amino acid sequence that has at least about 60% amino acid similarity, preferably at least about 70% amino acid similarity, and more preferably at least about 80% amino acid similarity to the amino acid sequences resulting from the translation of those nucleotide sequences present in FIG. 4. The present invention also includes purified peptides, polypeptides or proteins represented by these amino acid sequences which are, in turn, encoded by the above-described translated nucleotide sequences. For purposes of the present invention, "similarity" is defined as the exact amino acid to amino acid comparison of two or more polypeptides at the appropriate place, where amino acids are identical or possess similar chemical and/or physical properties such as charge or hydrophobicity. "Percent similarity" is calculated between the compared polypeptide sequences using programs known in the art (see above).

Transfection of the Sequence(s) into a Host Cell

One or more of the antisense oligonucleotides of Chk1, or fragments thereof, may be introduced into either a prokaryotic or eukaryotic host cell through the use of one or more transfection reagents in order to block Chk1 protein expression in the host cell.

The transfection reagent or vector, for example, a bacteriophage, cosmid or plasmid, may comprise full length Chk1 sense or antisense cDNA as well as any promoter which is functional in the host cell and is able to elicit expression of the peptide or protein encoded by the nucleotide sequence. The promoter is in operable association with or operably linked to the nucleotide sequence. (A promoter is said to be "operably linked" with a coding sequence if the promoter affects transcription or expression of the coding sequence.) Suitable promoters include, for example, CMV-based promoters (including but not limited to tetracyclin-regulated CMV promoters), the ecdysone-responsive promoter and the 5' LTR, for expression in mammalian cells, GL4 (galactose inducible) and ADH1, for expression in yeast, and T7, T3, Sp6 and Lac, for expression in bacteria.

Additionally, other nucleotide sequences may also be included within the vector as well as other regulatory sequences, for example, a replication origin which maintains the vector in the cells after dividing and/or an antibiotic resistance gene (e.g., an ampicillin resistance gene) which confers antibiotic resistance. The choice of sequences present in the construct or vector is dependent upon the desired expression product or products as well as the nature of the host cell.

Once the vector has been constructed, it may then be introduced into the host cell of choice (e.g., eukaryotic or prokaryotic) by methods known to those of ordinary skill in the art including, for example, transfection, transformation and electroporation (see *Molecular Cloning: A Laboratory Manual*, $2^{nd}$ ed., Vol. 1–3, ed. Sambrook et al., Cold Spring Harbor Press (1989)). Suitable examples of eukaryotic host cells include, for example, mammalian cells (e.g., human, rat and murine cells) and yeast cells. Human cells include, for example, primary cells (e.g., fibroblasts), immortalized cell lines (e.g., 184B5), and tumor cell lines (e.g., NCI-H1299, Hela cells, HCT116, MCF7, PC-3, A431 and SW684). Rat cells include, for example, primary cells, immortalized cell lines, and tumor cell lines (e.g., Matlylu). Mouse cells include, for example, primary cells, immortalized cells lines (e.g., NIH3T3). Suitable yeast cells include, for example, Saccharomyces spp. (e.g., *S. cerevisiae*) and Candida spp. (e.g., *C. albicans*).

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene product of interest can be selected for through the use of a selectable marker located on, or transfected with, the expression construct, followed by selection for cells expressing the marker. When stable expression results from integration, the site of the construct's integration may occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Uses of the Antisense Oligonucleotides of Chk1

The uses of the antisense oligonucleotides of the present invention are many. For example, the oligonucleotides, as noted above, may be introduced into a host cell in order to block translation of the nucleotide sequence encoding the Chk1 protein, thereby enhancing defects in tumor or malignant cells and causing specific killing of tumor cells.

In particular, the antisense oligonucleotides of the present invention, or fragments thereof, may also be used as pharmaceuticals which inhibit translation of the Chk1 protein. Thus, the pharmaceutical comprising one or more of the antisense oligonucleotides, will inhibit production of the protein thereby preventing G2 arrest of cells during chemotherapy or radiotherapy. Most chemotherapy reagents or radiotherapy induce DNA damage. Normally, cells will be arrested at both the G1 and G2 phase in order to repair DNA (Nurse et al., (1997) Cell 91:865–7). The majority of tumors have some defects in G1 checkpoints. Indeed, about 50% of tumor cells are defective in p53 function. Others have defects in other G1 checkpoint genes. Thus, G2 arrest is the only chance for the tumor cells to repair DNA. Inhibition of Chk1 protein expression will induce a defect in the G2 checkpoint. Thus, this mechanism impacts the tumor or malignant cells more profoundly than normal cells, thereby making them more sensitive to therapy (e.g., chemotherapy and radiation) as compared to normal cells. Consequently, specific killing of tumor cells will result, thereby maintaining the viability of healthy, normal cells in the patient and resulting in a better outcome. Thus, one may also increase the therapeutic window in this manner.

The pharmaceutical composition may comprise one or more of the antisense oligonucleotides or fragments thereof as well as a standard, well-known, non-toxic pharmaceutically acceptable, carrier, adjuvant or vehicle such as, for example, phosphate buffered saline (PBS), water, ethanol, a polyol, a vegetable oil, a wetting agent, or an emulsion such as a water/oil emulsion. The composition may be either in a liquid or solid form. For example, the composition may be in the form of a tablet, capsule or injectible. The dosage of the composition as well as the form may be readily determined by one of ordinary skill in the art.

In addition, the isolated nucleotide sequences of the present invention, as well as the related sequences described above with respect to sequence identity, may be used in order to create primers and probes. The probes may be used to detect nucleic acids in test samples, and the primers may be used for amplification purposes.

The design of such probes, for optimization in assays, is well within the knowledge of one of ordinary skill in the art. Generally, nucleic acid probes are developed from non-conserved regions when maximum specificity is desired, and nucleic acid probes are developed from conserved regions when assaying for nucleotide regions that are closely related to, for example, different members of a multi-gene family or in related species.

The probes (nucleotide sequences) of the present invention may be used, for example, to discover other antisense oligonucleotides related to those of the present invention. Thus, the probes would hybridize to portions of the Chk1 nucleotide sequence which may then be utilized, for example, for therapeutic purposes.

Primers may also be developed, using the antisense oligonucleotides of the present invention, for utilization in the polymerase chain reaction (PCR) (see U.S. Pat. No. 4,683,195 and U.S. Pat. No. 4,683,202). PCR is a technique for amplifying a desired nucleic acid sequence contained in a nucleic acid or mixture thereof. The primers are each extended by a polymerase using the target nucleic acid as a template. The extension products become target sequences, following dissociation from the original target strand. New primers are then hybridized and extended by a polymerase, and the cycle is repeated in order to increase the number of target sequence molecules.

The present invention also encompasses a method comprising blocking Chk1 expression by mammalian cells by transfecting vectors with polynucleotides that contain nucleic acid sequences with at least 40%, preferably at least 60% and more preferably at least 90% identity to the Chk1 antisense oligonucleotides of the present invention.

The present invention may be illustrated by the use of the following non-limiting examples:

Example I

Blocking of Chk1 Expression in Mammalian Cells Using Vectors Expressing Full Length Chk1 Antisense cDNA The coding regions of the full length Chk1 sense cDNA (see FIG. 8) and antisense cDNA were cloned in the pCMV5 or pCMV4 vector (Department of Molecular Genetics, University of Texas Southwestern Medical Center, Dallas, Tex.). Construction of pCMV1 and pCMV4 have been described in Anderson et al., *J. Biol. Chem.* 264:82222–9 (1988). To create pCMV5, a segment of DNA between HpaI and EcoRI restriction sites closest to the SV40 origin were deleted from pCMV1. The pCMV5 vector contains a CMV promoter which expresses the downstream gene in mammalian cells. Clones were confirmed by sequencing.

Since the expression level of a protein with a short half life is more likely to be reduced in a transient transfection experiment, the half life of Chk1 proteins was measured and determined to be 3–5 hours (FIG. 1). Transient transfection experiments were carried out to examine the effect of Chk1 antisense cDNA. In particular, NCI-H1299 cells (ATCC, Catalogue Number CRL-5803) were grown at 37° C. in a 5% $CO_2$ atmosphere in Roswell Park Memorial Institute 1640 (RPMI 1640 media) (Life Technologies, Gaithersburg, Md.) supplemented with 10% fetal bovine serum, 1 mM sodium pyruvate, 1 mM N-[2-Hydroxyethyl]piperazine-N'-[2-ethanesulfonic acid](HEPES), 1 mM glutamine, and 4 g/L glucose. The cells were then plated on 10 cm tissue culture plates the day before transfection and were 80% confluent at the time of transfection. Transfection was carried out according to the vendor's instructions (Life Technologies, Gaithersburg, Md.). In particular, 1.5 µg/ml of the appropriate DNA was mixed with lipofectamine plus reagent in 750 µl serum free RPMI 1640 media (solution I) (Life Technologies, Gathersburg, Md., Catalogue Number 10964–013) and incubated for 15 minutes at room temperature. Solution I was then added to a mixture containing lipofectamine reagent in 750 µl serum free RPMI 1640 media (solution II), mixed, incubated for an additional 15 minutes at room temperature to allow for DNA complexes to form. After the final 15 minute incubation, the NCI-H1299 cells that were to be transfected were washed once with Phosphate Buffered Saline (PBS), and 3.5 ml serum free media was added to each 10 cm dish. The mixture of solution I and solution II (transfection mixture) was then added dropwise to 3.5 ml of serum free RPMI 1640 that had already been added to the 10 cm tissue culture dish. The cells were incubated at 37° C. for 4 hours. After 4 hours of incubation, the transfection mixture was aspirated from the cells. The cells were then washed once with serum free media, and RPMI 1640 media (containing 10% fetal bovine serum, 1 mM sodium pyruvate, 1 mM HEPES, 1 mM glutamine, and 4 g/L glucose) was added to the tissue culture containing the transfected NCIOH1299 cells. At 24 hours post-transfection, the cells were harvested and subjected to Western blot analysis to assess antisense activity based upon the decrease in protein levels of Chk1.

Figure 2:
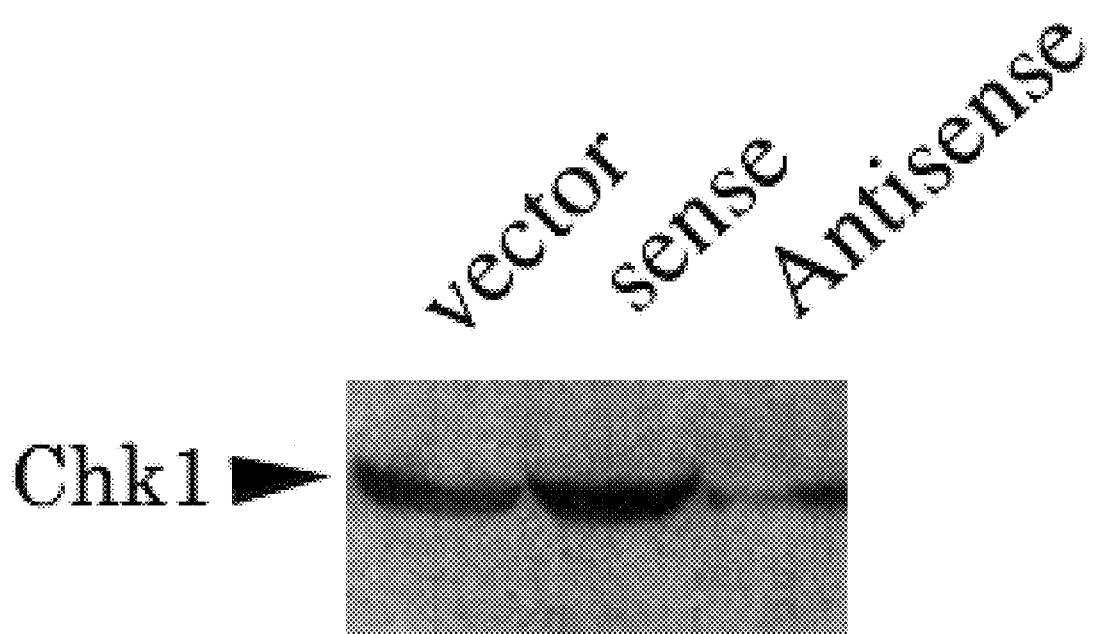
FIG. 2 illustrates Western blots showing expression of Chk1 in NCI-H1299 cells transfected with a vector containing full length sense or antisense Chk1 cDNA. Expression of Chk1 protein was two-fold over the endogenous level when transfected with Chk1 sense cDNA. Expression of the full length Chk1 antisense cDNA blocked about 50–70% of endogenous Chk1 expression.

Western blot analysis revealed that the expression of Chk1 sense cDNA resulted in about two-fold Chk1 expression compared with the endogenous level. In contrast, full length Chk1 antisense cDNA blocked about 50–70% of endogenous Chk1 expression (see FIG. 2).

Normally, *S. pombe* cells with Δ-chk1 alleles are viable except that they are defective in gamma irradiation-induced delay of mitosis in a weeI-50Δ-mikI background. An examination was made of the apoptosis rate of cells transfected with Chk1 antisense oligonucleotides or control oligonucleotides. Specifically, 24 hours after transfection, the cells were harvested by trypsinization, washed with PBS and stained with 2 µg/ml 4', 6-Diamidino-2-phenylindole (DAPI) stain (Sigma, St. Louis, Mo., Cat. Number D-8417). The apoptotic cells were scored on the basis of chromosomal condensation and fragmentation. At least 600 cells were examined for each data point.

Figure 3:
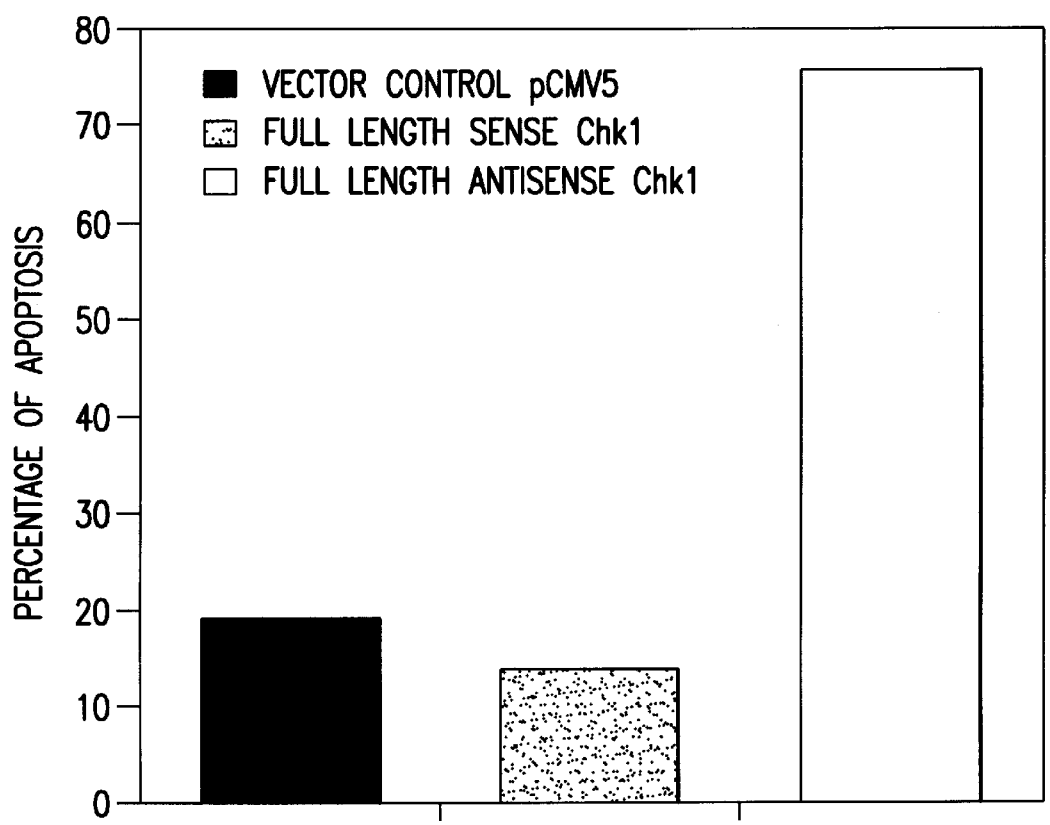
FIG. 3 illustrates the percent of cells that died when Chk1 expression was blocked as a result of transfection with a vector expressing Chk1 antisense cDNA. The expression of Chk1 sense cDNA moderately protected the transfected cells from cell death.
Figure 5:
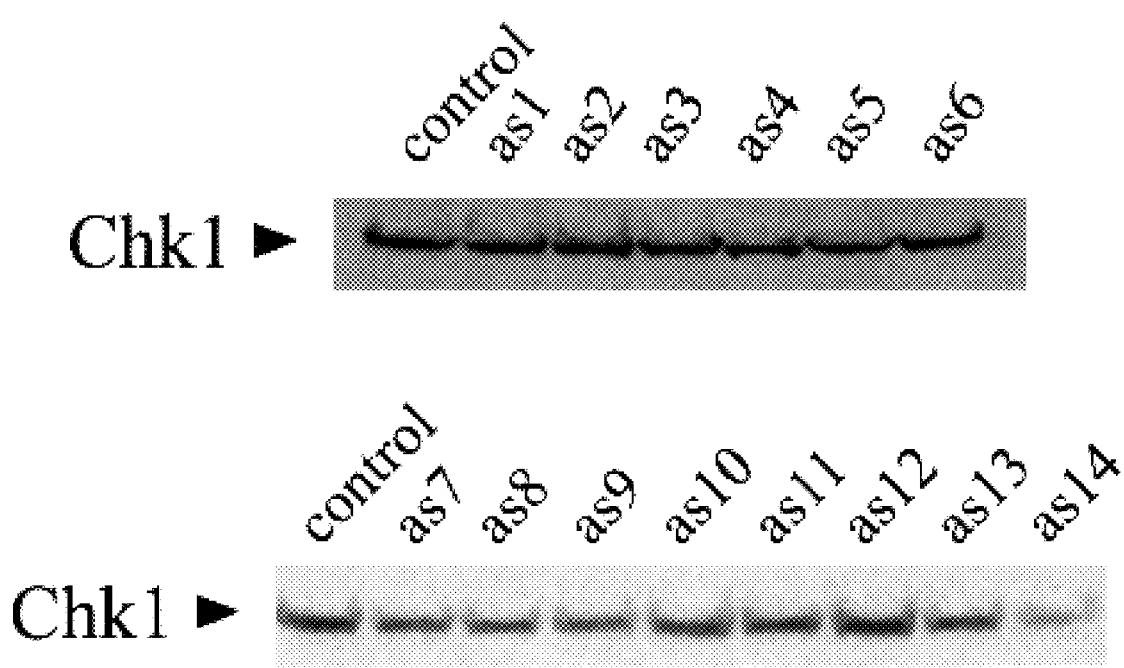
FIG. 5 illustrates the level of Chk1 expression in cells transfected with antisense oligonucleotides 1 (SEQ ID NO:5), 2 (SEQ ID NO:6), 3 (SEQ ID NO:7), 4 (SEQ ID NO:8), 5 (SEQ ID NO:9), 6 (SEQ ID NO:10), 7 (SEQ ID NO:1), 8 (SEQ ID NO:2), 9 (SEQ ID NO:3), 10 (SEQ ID NO:11), 11 (SEQ ID NO:12), 12 (SEQ ID NO:13), 13 (SEQ ID NO:14) and 14 (SEQ ID NO:4). Chk1 expression was blocked significantly in cells transfected with oligonucleotides 7, 8, 9 and 14.

Cell death in NCI-H1299 cells was observed as a consequence of reduced Chk1 protein levels. In contrast, cells exhibiting a two-fold increase in Chk1 protein expression, due to Chk1 cDNA expression, were protected moderately from cell death (see FIG. 3). The same results were also observed in Hela cells (data not shown).

EXAMPLE II

Blocking of Chk1 Expression in Mammalian Cells By Use of Antisense Oligonucleotides Antisense oligonucleotides of Chk1 were designed so that they consisted of 19 nucleotides with a core of 9 phosphothiol-substituted nucleotides flanked by five 2-O-methyl-substituted nucleotides at each end. The sequences of the oligonucleotides are shown in FIG. 4. In particular, antisense oligonucleotides 7, 8, 9, and 10 were designed to hybridize to the region of the Chk1 nucleotide sequence around the ATG start codon. Antisense oligonucleotides 11, 12, 13 and 14 were designed to hybridize to different sites of the coding region that contain a GGGA sequence.

The day before transfection, NCI-H1299 cells were seeded onto a 10 cm tissue culture plate at a density of $1.3 \times 10^6$/dish. On the day of antisense oligonucleotide transfection, the density of NCI-H1299 cells reached $2.6 \times 10^6$ or 80% confluence per 10 cm dish. 1 µM of the appropriate Chk1 antisense oligonucleotide was co-incubated with 4 µg/ml of the cytofectin GSV transfection reagent (Glen Research, Sterlilng, Va., Catalogue Number G810502) at room temperature for 15 minutes. The DNA complex solution was then added dropwise to the cells as previously described (Wagner et al., *Nature* 372: 333–5 (1994)). At 24 hours post-transfection, NCI-H1299 cells were harvested and subjected to Western blot analysis to assess antisense activity based on the decrease in protein levels of Chk1.

Antisense oligonucleotides 7, 8, 9 and 14 reduced about 50% of Chk1 protein expression. Furthermore, since Chk1 full-length antisense cDNA blocked Chk1 expression and the decreased level of Chk1 protein resulted in cell death, Chk1 antisense oligonucleotides 7, 8, 9 and 14 may also induce cell death.

EXAMPLE III

Response of Transfected Cells to Adriamycin

It has been shown that Chk1 is phosphorylated and activated upon DNA damage (Walworth et al., *Science* 271:353–56 (1996)). Given that Chk1 can phosphorylate and inactivate Cdc25C which is required for Cdc2 activation, Chk1 has been thought to be involved in the DNA damage response in mammalian cells. (*S. pombe* Chk1 is required for G2 arrest induced by DNA damaging reagents.)

In the present experiment, the effect of adriamycin on transfected cells was examined. A milder transfection reagent Lipofectamine 2000 (Life Technologies, Gaithersburg, Md.), Cat. Number 11668–019) was used in the following experiments in an effort to decrease the extent of cells death of the transfected cells in order to adequately observe the effect of adriamycin. As a result of using the Lipofectamine 2000 transfection reagent, transfection efficiency decreased by about 10%; however, the transfected cells responded much better to adriamcyin and etoposide treatment 24 hours after transfection compared to lipofectamine plus transfected cells (data not shown). In particular, NCI-H1299 cells were treated with 300 ng/ml of adriamycin 24 hours after transfection. Eight hours after exposure to adriamycin, 40 ng/ml of nocodazole was added to the transfected cells in order to trap any cells that escaped G2 arrest induced by adriamcyin. Sixteen hours after the nocodazole treatment, cells were harvested by trypsinization. The cells were then washed with PBS, swelled with hypotonic buffer containing 75 µM KCl, and stained using the Diff-qwik stain set according to the vendor's instructions (Dade Behring, Inc., Newark, Del., Cat. Number B4132–2). Mitotic cells were scored based upon the chromosomal condensation and the disappearance of the nuclear membrane. At least 600 cells were counted for each data point.

Figure 6:
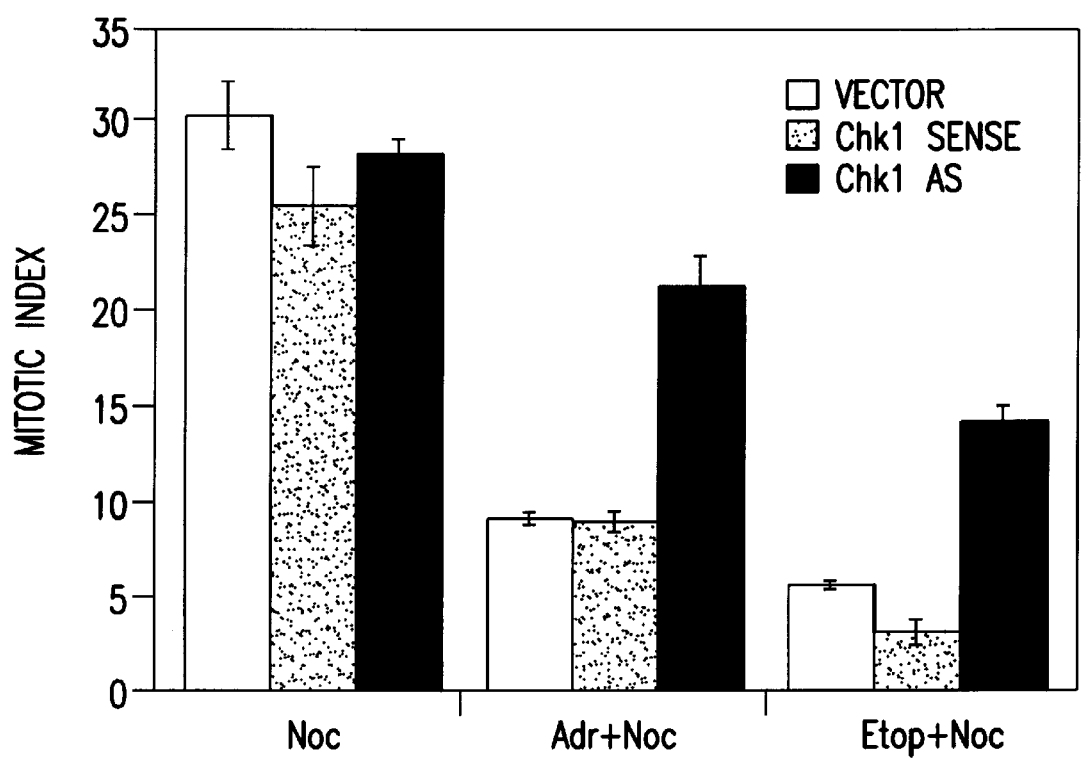
FIG. 6 illustrates the percentage of cells that escaped from the G2 arrest induced by DNA damaging reagents. More of the full length Chk1 antisense cDNA transfected cells escaped the G2 arrest than that of vector transfected cells.

The mitotic index of cells that were transfected with Chk1 antisense CDNA was much higher than that of cells transfected with either vector control or Chk1 sense cDNA (FIG. 6). This indicated that more antisense transfectants progressed through the G2/M boundary without being arrested than as compared to the vector transfected cells. Thus, a decreased Chk1 protein level resulted in a defect in G2 arrest during the damage response.

It is expected that the antisense oligonucleotide transfected cells would show a similar phenotype to the cells transfected with full-length antisense Chk1 cDNA discussed above.

EXAMPLE IV

Apoptosis Rate of Chk1 Sense and Antisense cDNA Transfected Cells Upon Treatment With Adriamycin The apoptosis rate of full-length sense or antisense Chk1 cDNA transfected cells treated with adriamycin was examined. In particular, 24 hours after transfection, the transfected NCI-H1299 cells were treated with 600 ng/ml of adriamycin for 48 hours. The cells were then harvested by trypsinization, washed once with PBS and stained with 2 µg/ml DAPI. The apoptotic cells were then scored on the basis of chromosomal condensation and fragmentation. In particular, at least 600 cells were examined for each data point.

Figure 7:
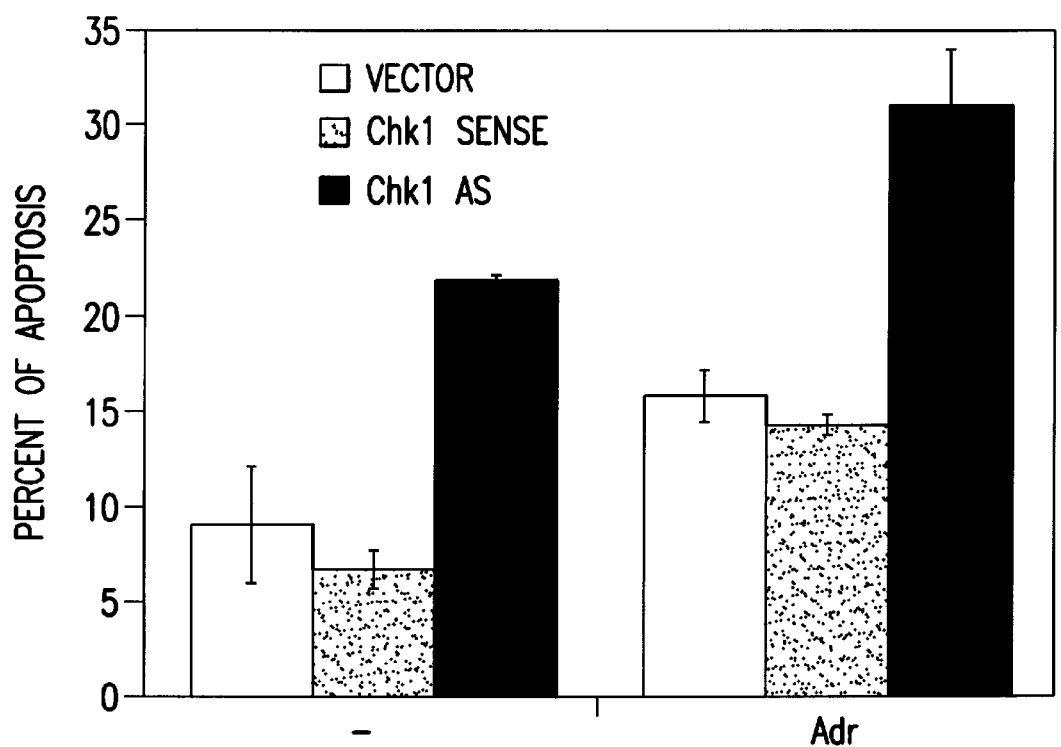
FIG. 7 illustrates the percentage of cell death induced by adriamycin and Chk1 full length antisense cDNA transfection. The cell death caused by adriamycin is additive to that induced by Chk1 full length antisense cDNA transfection.

Adriamycin killed tumor cells in addition to the killing effect of Chk1 antisense cDNA. The synergy between adriamycin and Chk1 antisense cDNA is weak if any (see FIG. 7). (The same results are expected in connection with the Chk1 antisense oligonucleotides.)

This experiment may also be done utilizing a pair of cell lines that differ only in their G1 checkpoint status. Such cell lines would mimic normal cells and tumor cells since most tumor cells are defective in the G1 checkpoint. Such an experiment would uncover whether an inhibitor of Chk1 may confer specific sensitization of tumors being treated with cancer therapy.

What is claimed is:

1. An isolated antisense nucleotide sequence of a mammalian Chk1 gene which inhibits expression of Chk1 protein, wherein said nucleotide sequence has at least 40% identity to a sequence selected from the group consisting of 1) SEQ ID NO:1, 2) SEQ ID NO:2, 3) SEQ ID NO:3, 4) SEQ ID NO:4, and 5) a fragment of SEQ ID NO:1, SEQ ID NO:2, SEQ ID NO:3 and SEQ ID NO:4 which specifically hybridizes to the complement of SEQ ID NO:1, SEQ ID NO:2, SEQ ID NO:3 or SEQ ID NO:4, respectively.

2. An isolated nucleotide sequence having at least 40% identity to SEQ ID NO:1 or a fragment of said isolated nucleotide sequence which specifically hybridizes to the complement of said isolated nucleotide sequence.

3. An isolated nucleotide sequence having at least 40% identity to SEQ ID NO:2 or a fragment of said sequence which specifically hybridizes to the complement of said isolated nucleotide sequence.

4. An isolated nucleotide sequence having at least 40% identity to SEQ ID NO:3 or a fragment of said sequence which specifically hybridizes to the complement of said isolated nucleotide sequence.

5. An isolated nucleotide sequence having at least 40% identity to SEQ ID NO:4.

6. A method of preventing in vitro expression of Chk1 protein by a cell comprising the step of introducing into said cell a vector comprising said nucleotide sequence of claim 1.

7. A method of preventing in vitro expression of Chk1 protein by a cell comprising the step of introducing into said cell a vector comprising an isolated nucleotide sequence having at least 40% identity to a nucleotide sequence selected from the group consisting of SEQ ID NO:1, SEQ ID NO:2, SEQ ID NO:3 and SEQ ID NO:4, or a fragment of said isolated nucleotide sequence which specifically hybridizes to the complement of said isolated nucleotide sequence.

8. A method of screening a compound for ability to inhibit endogenous expression of Chk1 protein by a cell comprising the steps of exposing said cell to said compound and measuring expression of Chk1 protein by said cell, lack of expression of Chk1 protein indicating a compound having the ability to inhibit expression of Chk1 protein.

9. A method of sensitizing malignant cells to chemotherapy, in vitro, comprising the step of exposing said cells to an amount of the pharmaceutical composition of claims 8 or 10 effective to cause said sensitization.

* * * * *

UNITED STATES PATENT AND TRADEMARK OFFICE
CERTIFICATE OF CORRECTION

PATENT NO.    : 6,211,164 B1
DATED         : April 3, 2001
INVENTOR(S)   : Yan Luo et al.

It is certified that error appears in the above-identified patent and that said Letters Patent is hereby corrected as shown below:

Column 23,
Line 9, replace "antisense nucleotide sequence of a mammalian Chkl gene" with -- antisense oligonucleotide of at least 6 nucleotides in length targeting human Chkl gene. --
Line 11, replace "wherein. said nucleotide sequence has at least 40% identity " with -- wherein said antisense oligonucleotide has at least 40% identity --.
Line 18, replace "An isolated nucleotide sequence having at least 40%" with -- The antisense oligonucleotde of claim 1 having at least 40% --.
Line 19-20, replace "of said isolated nucleotide sequence which specifically " with -- of said antisense oligonuclecotde which specifically --.
Line 21, replace "complement of said isolated nucleotide sequence. " with -- complement of said antisense oligonucleotide. --.
Line 22, replace "An isolated nucleotide sequence having at least 40%" with -- The antisense oligonucleotide of claim 1 having at least 40% --.
Line 23-24, replace "said sequence which specifically hybridizes to the complement" with -- "said antisense oligonucleotide which specificaly hybridizes to the complement --.
Line 24-25, replace ""said isolated nucleotide sequence."" with -- said antisense oligonucleotide. --.
Line 26, replace "An isolated nucleotide sequence having"" with --The antisense oligonucleotide of claim 1 having" --.
Line 27-28, replace "of said sequence which specifically" with --of said antisense oligonucleotide which specifically --.
Line 29, replace "isolated nucleotide sequence." with -- antisense oligonucleotide. --.
Line 30, replace "An isolated nucleotide sequence having" with -- The antisense oligonucleotide of claim 1 having --.

Column 24,
Line 8, replace "expression of Chkl" with -- expression of human Chkl --.
Line 10, replace "vector comprising said nucleotide sequence of " with -- vector comprising said antisense oligonucleotide of --.
Line 12-13, replace "of Chkl protein by a cell" with -- of human Chkl protein by a cell --.
Line 14, replace "an isolated nucleotide sequence having " with --an antisense oligonucleotid having--.

UNITED STATES PATENT AND TRADEMARK OFFICE
CERTIFICATE OF CORRECTION

PATENT NO.   : 6,211,164 B1
DATED        : April 3, 2001
INVENTOR(S)  : Yan Luo et al.

It is certified that error appears in the above-identified patent and that said Letters Patent is hereby corrected as shown below:

<u>Column 24 (continued),</u>
Line 18, replace "said isolated nucleotide sequence which" with -- said antisense oligonucleotide which --.
Line 19, replace "said isolated nucleotide sequence." with -- said antisense oligonucleotide, thereby preventing the expression of human Chkl protein in said cell. --
Line 28-29, replace ""of the pharmaceutical composition of claims 8 or 10 effective" with -- of the composition of claim 8 effective. --.
Line 10-25, replace "A method of screening a compound for ability to inhibit endogenous expression of Chk1 protein by a cell comprising the steps of exposing said cell to said compound and measuring expression of Chk1 protein by said cell lack of expression of Chk1 protein." with -- "A composition ocmprising said antisense oligonucleotide of claim 1 and a pharmaceutically acceptable carrier. --

Signed and Sealed this

Twenty-fifth Day of June, 2002

Attest:

Attesting Officer

JAMES E. ROGAN
*Director of the United States Patent and Trademark Office*

SEQUENCE LISTING

```
<160> NUMBER OF SEQ ID NOS:  17

<210> SEQ ID NO 1
<211> LENGTH: 19
<212> TYPE: DNA
<213> ORGANISM: Artificial Sequence
<220> FEATURE:
<223> OTHER INFORMATION: CHK1-as7
```

```
<400> SEQUENCE: 1
cgagcaccuc ggcggacug                                                  19

<210> SEQ ID NO 2
<211> LENGTH: 19
<212> TYPE: DNA
<213> ORGANISM: Artificial Sequence
<220> FEATURE:
<223> OTHER INFORMATION: CHK1-as8

<400> SEQUENCE: 2
gccaugacuc caccgagca                                                  19

<210> SEQ ID NO 3
<211> LENGTH: 19
<212> TYPE: DNA
<213> ORGANISM: Artificial Sequence
<220> FEATURE:
<223> OTHER INFORMATION: CHK1-as9

<400> SEQUENCE: 3
ggcacugcca ugacuccac                                                  19

<210> SEQ ID NO 4
<211> LENGTH: 19
<212> TYPE: DNA
<213> ORGANISM: Artificial Sequence
<220> FEATURE:
<223> OTHER INFORMATION: CHK1-as14

<400> SEQUENCE: 4
gguugguccc auggcaauu                                                  19

<210> SEQ ID NO 5
<211> LENGTH: 19
<212> TYPE: DNA
<213> ORGANISM: Artificial Sequence
<220> FEATURE:
<223> OTHER INFORMATION: CHK1-as1

<400> SEQUENCE: 5
uuacucuauu cacagcaag                                                  19

<210> SEQ ID NO 6
<211> LENGTH: 19
<212> TYPE: DNA
<213> ORGANISM: Artificial Sequence
<220> FEATURE:
<223> OTHER INFORMATION: CHK1-as2

<400> SEQUENCE: 6
aguugaugga agaaucucu                                                  19

<210> SEQ ID NO 7
<211> LENGTH: 19
<212> TYPE: DNA
<213> ORGANISM: Artificial Sequence
<220> FEATURE:
<223> OTHER INFORMATION: CHK1-as3

<400> SEQUENCE: 7
gagguuaucc cuuucaucc                                                  19

<210> SEQ ID NO 8
<211> LENGTH: 19
```

```
<212> TYPE: DNA
<213> ORGANISM: Artificial Sequence
<220> FEATURE:
<223> OTHER INFORMATION: CHK1-as4

<400> SEQUENCE: 8
caagccaaag ucugagauu                                                19

<210> SEQ ID NO 9
<211> LENGTH: 19
<212> TYPE: DNA
<213> ORGANISM: Artificial Sequence
<220> FEATURE:
<223> OTHER INFORMATION: CHK1-as5

<400> SEQUENCE: 9
uucucuucuc uucagaagu                                                19

<210> SEQ ID NO 10
<211> LENGTH: 19
<212> TYPE: DNA
<213> ORGANISM: Artificial Sequence
<220> FEATURE:
<223> OTHER INFORMATION: CHK1-as6

<400> SEQUENCE: 10
augaaauucu cuucucuuc                                                19

<210> SEQ ID NO 11
<211> LENGTH: 19
<212> TYPE: DNA
<213> ORGANISM: Artificial Sequence
<220> FEATURE:
<223> OTHER INFORMATION: CHK1-as10

<400> SEQUENCE: 11
cacaaagggc acugccaug                                                19

<210> SEQ ID NO 12
<211> LENGTH: 19
<212> TYPE: DNA
<213> ORGANISM: Artificial Sequence
<220> FEATURE:
<223> OTHER INFORMATION: CHK1-as11

<400> SEQUENCE: 12
caccaagucc cagucuucc                                                19

<210> SEQ ID NO 13
<211> LENGTH: 19
<212> TYPE: DNA
<213> ORGANISM: Artificial Sequence
<220> FEATURE:
<223> OTHER INFORMATION: CHK1-as12

<400> SEQUENCE: 13
gcaccuucuc ccaggguuu                                                19

<210> SEQ ID NO 14
<211> LENGTH: 19
<212> TYPE: DNA
<213> ORGANISM: Artificial Sequence
<220> FEATURE:
<223> OTHER INFORMATION: CHK1-as13
```

<400> SEQUENCE: 14
uuuaauaucc cugugaguu                                                19

<210> SEQ ID NO 15
<211> LENGTH: 1821
<212> TYPE: DNA
<213> ORGANISM: Homo sapiens
<220> FEATURE:
<221> NAME/KEY: CDS
<222> LOCATION: (35)...(1463)

<400> SEQUENCE: 15

```
ggccggacag tccgccgagg tgctcggtgg agtc atg gca gtg ccc ttt gtg gaa      55
                                    Met Ala Val Pro Phe Val Glu
                                      1               5 gac tgg gac ttg gtg caa acc ctg gga gaa ggt gcc tat gga gaa gtt      103
Asp Trp Asp Leu Val Gln Thr Leu Gly Glu Gly Ala Tyr Gly Glu Val
         10                  15                  20 caa ctt gct gtg aat aga gta act gaa gaa gca gtc gca gtg aag att      151
Gln Leu Ala Val Asn Arg Val Thr Glu Glu Ala Val Ala Val Lys Ile
 25                  30                  35 gta gat atg aag cgt gcc gta gac tgt cca gaa aat att aag aaa gag      199
Val Asp Met Lys Arg Ala Val Asp Cys Pro Glu Asn Ile Lys Lys Glu
 40                  45                  50                  55 atc tgt atc aat aaa atg cta aat cat gaa aat gta gta aaa ttc tat      247
Ile Cys Ile Asn Lys Met Leu Asn His Glu Asn Val Val Lys Phe Tyr
                 60                  65                  70 ggt cac agg aga gaa ggc aat atc caa tat tta ttt ctg gag tac tgt      295
Gly His Arg Arg Glu Gly Asn Ile Gln Tyr Leu Phe Leu Glu Tyr Cys
             75                  80                  85 agt gga gga gag ctt ttt gac aga ata gag cca gac ata ggc atg cct      343
Ser Gly Gly Glu Leu Phe Asp Arg Ile Glu Pro Asp Ile Gly Met Pro
         90                  95                 100 gaa cca gat gct cag aga ttc ttc cat caa ctc atg gca ggg gtg gtt      391
Glu Pro Asp Ala Gln Arg Phe Phe His Gln Leu Met Ala Gly Val Val
    105                 110                 115 tat ctg cat ggt att gga ata act cac agg gat att aaa cca gaa aat      439
Tyr Leu His Gly Ile Gly Ile Thr His Arg Asp Ile Lys Pro Glu Asn
120                 125                 130                 135 ctt ctg ttg gat gaa agg gat aac ctc aaa atc tca gac ttt ggc ttg      487
Leu Leu Leu Asp Glu Arg Asp Asn Leu Lys Ile Ser Asp Phe Gly Leu
                140                 145                 150 gca aca gta ttt cgg tat aat aat cgt gag cgt ttg ttg aac aag atg      535
Ala Thr Val Phe Arg Tyr Asn Asn Arg Glu Arg Leu Leu Asn Lys Met
            155                 160                 165 tgt ggt act tta cca tat gtt gct cca gaa ctt ctg aag aga aga gaa      583
Cys Gly Thr Leu Pro Tyr Val Ala Pro Glu Leu Leu Lys Arg Arg Glu
        170                 175                 180 ttt cat gca gaa cca gtt gat gtt tgg tcc tgt gga ata gta ctt act      631
Phe His Ala Glu Pro Val Asp Val Trp Ser Cys Gly Ile Val Leu Thr
    185                 190                 195 gca atg ctc gct gga gaa ttg cca tgg gac caa ccc agt gac agc tgt      679
Ala Met Leu Ala Gly Glu Leu Pro Trp Asp Gln Pro Ser Asp Ser Cys
200                 205                 210                 215 cag gag tat tct gac tgg aaa gaa aaa aaa aca tac ctc aac cct tgg      727
Gln Glu Tyr Ser Asp Trp Lys Glu Lys Lys Thr Tyr Leu Asn Pro Trp
                220                 225                 230 aaa aaa atc gat tct gct cct cta gct ctg ctg cat aaa atc tta gtt      775
Lys Lys Ile Asp Ser Ala Pro Leu Ala Leu Leu His Lys Ile Leu Val
            235                 240                 245
```

-continued

| | | |
|---|---|---|
| gag aat cca tca gca aga att acc att cca gac atc aaa aaa gat aga<br>Glu Asn Pro Ser Ala Arg Ile Thr Ile Pro Asp Ile Lys Lys Asp Arg<br>250 255 260 | 823 |
| tgg tac aac aaa ccc ctc aag aaa ggg gca aaa agg ccc cga gtc act<br>Trp Tyr Asn Lys Pro Leu Lys Lys Gly Ala Lys Arg Pro Arg Val Thr<br>265 270 275 | 871 |
| tca ggt ggt gtg tca gag tct ccc agt gga ttt tct aag cac att caa<br>Ser Gly Gly Val Ser Glu Ser Pro Ser Gly Phe Ser Lys His Ile Gln<br>280 285 290 295 | 919 |
| tcc aat ttg gac ttc tct cca gta aac agt gct tct agt gaa gaa aat<br>Ser Asn Leu Asp Phe Ser Pro Val Asn Ser Ala Ser Ser Glu Glu Asn<br>300 305 310 | 967 |
| gtg aag tac tcc agt tct cag cca gaa ccc cgc aca ggt ctt tcc tta<br>Val Lys Tyr Ser Ser Ser Gln Pro Glu Pro Arg Thr Gly Leu Ser Leu<br>315 320 325 | 1015 |
| tgg gat acc agc ccc tca tac att gat aaa ttg gta caa ggg atc agc<br>Trp Asp Thr Ser Pro Ser Tyr Ile Asp Lys Leu Val Gln Gly Ile Ser<br>330 335 340 | 1063 |
| ttt tcc cag ccc aca tgt cct gat cat atg ctt ttg aat agt cag tta<br>Phe Ser Gln Pro Thr Cys Pro Asp His Met Leu Leu Asn Ser Gln Leu<br>345 350 355 | 1111 |
| ctt ggc acc cca gga tcc tca cag aac ccc tgg cag cgg ttg gtc aaa<br>Leu Gly Thr Pro Gly Ser Ser Gln Asn Pro Trp Gln Arg Leu Val Lys<br>360 365 370 375 | 1159 |
| aga atg aca cga ttc ttt acc aaa ttg gat gca gac aaa tct tat caa<br>Arg Met Thr Arg Phe Phe Thr Lys Leu Asp Ala Asp Lys Ser Tyr Gln<br>380 385 390 | 1207 |
| tgc ctg aaa gag act tgt gag aag ttg ggc tat caa tgg aag aaa agt<br>Cys Leu Lys Glu Thr Cys Glu Lys Leu Gly Tyr Gln Trp Lys Lys Ser<br>395 400 405 | 1255 |
| tgt atg aat cag gtt act ata tca aca act gat agg aga aac aat aaa<br>Cys Met Asn Gln Val Thr Ile Ser Thr Thr Asp Arg Arg Asn Asn Lys<br>410 415 420 | 1303 |
| ctc att ttc aaa gtg aat ttg tta gaa atg gat gat aaa ata ttg gtt<br>Leu Ile Phe Lys Val Asn Leu Leu Glu Met Asp Asp Lys Ile Leu Val<br>425 430 435 | 1351 |
| gac ttc cgg ctt tct aag ggt gat gga ttg gag ttc aag aga cac ttc<br>Asp Phe Arg Leu Ser Lys Gly Asp Gly Leu Glu Phe Lys Arg His Phe<br>440 445 450 455 | 1399 |
| ctg aag att aaa ggg aag ctg att gat att gtg agc agc cag aag gtt<br>Leu Lys Ile Lys Gly Lys Leu Ile Asp Ile Val Ser Ser Gln Lys Val<br>460 465 470 | 1447 |
| tgg ctt cct gcc aca t gatcggacca tcggctctgg ggaatcctgg tgaatatagt<br>Trp Leu Pro Ala Thr<br>475 | 1503 |
| gctgctatgt tgacattatt cttcctagag aagattatcc tgtcctgcaa actgcaaata | 1563 |
| gtagttcctg aagtgttcac ttccctgttt atccaaacat cttccaattt attttgtttg | 1623 |
| ttcggcatac aaataatacc tatatcttaa ttgtaagcaa aactttgggg aaaggatgaa | 1683 |
| tagaattcat ttgattattt cttcatgtgt gtttagtatc tgaatttgaa actcatctgg | 1743 |
| tggaaaccaa gtttcagggg acatgagttt tccagctttt atacacacgt atctcatttt | 1803 |
| tatcaaaaca ttttgttt | 1821 |

<210> SEQ ID NO 16
<211> LENGTH: 476
<212> TYPE: PRT
<213> ORGANISM: Homo sapiens -continued

```
<400> SEQUENCE: 16

Met Ala Val Pro Phe Val Glu Asp Trp Asp Leu Val Gln Thr Leu Gly
 1               5                  10                  15

Glu Gly Ala Tyr Gly Glu Val Gln Leu Ala Val Asn Arg Val Thr Glu
            20                  25                  30

Glu Ala Val Ala Val Lys Ile Val Asp Met Lys Arg Ala Val Asp Cys
        35                  40                  45

Pro Glu Asn Ile Lys Lys Glu Ile Cys Ile Asn Lys Met Leu Asn His
    50                  55                  60

Glu Asn Val Val Lys Phe Tyr Gly His Arg Arg Glu Gly Asn Ile Gln
 65                  70                  75                  80

Tyr Leu Phe Leu Glu Tyr Cys Ser Gly Gly Glu Leu Phe Asp Arg Ile
                85                  90                  95

Glu Pro Asp Ile Gly Met Pro Glu Pro Asp Ala Gln Arg Phe Phe His
            100                 105                 110

Gln Leu Met Ala Gly Val Val Tyr Leu His Gly Ile Gly Ile Thr His
        115                 120                 125

Arg Asp Ile Lys Pro Glu Asn Leu Leu Leu Asp Glu Arg Asp Asn Leu
    130                 135                 140

Lys Ile Ser Asp Phe Gly Leu Ala Thr Val Phe Arg Tyr Asn Asn Arg
145                 150                 155                 160

Glu Arg Leu Leu Asn Lys Met Cys Gly Thr Leu Pro Tyr Val Ala Pro
                165                 170                 175

Glu Leu Leu Lys Arg Arg Glu Phe His Ala Glu Pro Val Asp Val Trp
            180                 185                 190

Ser Cys Gly Ile Val Leu Thr Ala Met Leu Ala Gly Glu Leu Pro Trp
        195                 200                 205

Asp Gln Pro Ser Asp Ser Cys Gln Glu Tyr Ser Asp Trp Lys Glu Lys
    210                 215                 220

Lys Thr Tyr Leu Asn Pro Trp Lys Lys Ile Asp Ser Ala Pro Leu Ala
225                 230                 235                 240

Leu Leu His Lys Ile Leu Val Glu Asn Pro Ser Ala Arg Ile Thr Ile
                245                 250                 255

Pro Asp Ile Lys Lys Asp Arg Trp Tyr Asn Lys Pro Leu Lys Lys Gly
            260                 265                 270

Ala Lys Arg Pro Arg Val Thr Ser Gly Gly Val Ser Glu Ser Pro Ser
        275                 280                 285

Gly Phe Ser Lys His Ile Gln Ser Asn Leu Asp Phe Ser Pro Val Asn
    290                 295                 300

Ser Ala Ser Ser Glu Glu Asn Val Lys Tyr Ser Ser Ser Gln Pro Glu
305                 310                 315                 320

Pro Arg Thr Gly Leu Ser Leu Trp Asp Thr Ser Pro Ser Tyr Ile Asp
                325                 330                 335

Lys Leu Val Gln Gly Ile Ser Phe Ser Gln Pro Thr Cys Pro Asp His
            340                 345                 350

Met Leu Leu Asn Ser Gln Leu Leu Gly Thr Pro Gly Ser Ser Gln Asn
        355                 360                 365

Pro Trp Gln Arg Leu Val Lys Arg Met Thr Arg Phe Phe Thr Lys Leu
    370                 375                 380

Asp Ala Asp Lys Ser Tyr Gln Cys Leu Lys Glu Thr Cys Glu Lys Leu
385                 390                 395                 400

Gly Tyr Gln Trp Lys Lys Ser Cys Met Asn Gln Val Thr Ile Ser Thr
                405                 410                 415
```

-continued

```
Thr Asp Arg Arg Asn Asn Lys Leu Ile Phe Lys Val Asn Leu Leu Glu
            420                 425                 430

Met Asp Asp Lys Ile Leu Val Asp Phe Arg Leu Ser Lys Gly Asp Gly
        435                 440                 445

Leu Glu Phe Lys Arg His Phe Leu Lys Ile Lys Gly Lys Leu Ile Asp
    450                 455                 460

Ile Val Ser Ser Gln Lys Val Trp Leu Pro Ala Thr
465                 470                 475

<210> SEQ ID NO 17
<211> LENGTH: 1821
<212> TYPE: DNA
<213> ORGANISM: Homo sapiens

<400> SEQUENCE: 17
```

| | | | | | |
|---|---|---|---|---|---|
| aaacaaaatg | ttttgataaa | aatgagatac | gtgtgtataa | aagctggaaa | actcatgtcc | 60 |
| cctgaaactt | ggtttccacc | agatgagttt | caaattcaga | tactaaacac | acatgaagaa | 120 |
| ataatcaaat | gaattctatt | catcctttcc | ccaaagtttt | gcttacaatt | aagatatagg | 180 |
| tattatttgt | atgccgaaca | aacaaaataa | attggaagat | gtttggataa | acagggaagt | 240 |
| gaacacttca | ggaactacta | tttgcagttt | gcaggacagg | ataatcttct | ctaggaagaa | 300 |
| taatgtcaac | atagcagcac | tatattcacc | aggattcccc | agagccgatg | gtccgatcat | 360 |
| gtggcaggaa | gccaaacctt | ctggctgctc | acaatatcaa | tcagcttccc | tttaatcttc | 420 |
| aggaagtgtc | tcttgaactc | caatccatca | cccttagaaa | gccggaagtc | aaccaatatt | 480 |
| ttatcatcca | tttctaacaa | attcactttg | aaaatgagtt | tattgtttct | cctatcagtt | 540 |
| gttgatatag | taacctgatt | catacaactt | ttcttccatt | gatagcccaa | cttctcacaa | 600 |
| gtctctttca | ggcattgata | agatttgtct | gcatccaatt | tggtaaagaa | tcgtgtcatt | 660 |
| cttttgacca | accgctgcca | ggggttctgt | gaggatcctg | gggtgccaag | taactgacta | 720 |
| ttcaaaagca | tatgatcagg | acatgtgggc | tgggaaaagc | tgatcccttg | taccaattta | 780 |
| tcaatgtatg | aggggctggt | atcccataag | gaaagacctg | tgcggggttc | tggctgagaa | 840 |
| ctggagtact | tcacattttc | ttcactagaa | gcactgttta | ctggagagaa | gtccaaattg | 900 |
| gattgaatgt | gcttagaaaa | tccactggga | gactctgaca | caccacctga | agtgactcgg | 960 |
| ggccttttg | cccctttctt | gagggggtttg | ttgtaccatc | tatctttttt | gatgtctgga | 1020 |
| atggtaattc | ttgctgatgg | attctcaact | aagatttat | gcagcagagc | tagaggagca | 1080 |
| gaatcgattt | ttttccaagg | gttgaggtat | gtttttttttt | ctttccagtc | agaatactcc | 1140 |
| tgacagctgt | cactgggttg | gtcccatggc | aattctccag | cgagcattgc | agtaagtact | 1200 |
| attccacagg | accaaacatc | aactggttct | gcatgaaatt | ctcttctctt | cagaagttct | 1260 |
| ggagcaacat | atggtaaagt | accacacatc | ttgttcaaca | aacgctcacg | attattatac | 1320 |
| cgaaatactg | ttgccaagcc | aaagtctgag | attttgaggt | tatccctttc | atccaacaga | 1380 |
| agattttctg | gtttaatatc | cctgtgagtt | attccaatac | catgcagata | aaccacccct | 1440 |
| gccatgagtt | gatggaagaa | tctctgagca | tctggttcag | gcatgcctat | gtctggctct | 1500 |
| attctgtcaa | aaagctctcc | tccactacag | tactccagaa | ataaatattg | gatattgcct | 1560 |
| tctctccctgt | gaccatagaa | ttttactaca | ttttcatgat | ttagcatttt | attgatacag | 1620 |
| atctctttct | taatattttc | tggacagtct | acggcacgct | tcatatctac | aatcttcact | 1680 |
| gcgactgctt | cttcagttac | tctattcaca | gcaagttgaa | cttctccata | ggcaccttct | 1740 |

-continued

```
cccagggttt gcaccaagtc ccagtcttcc acaaagggca ctgccatgac tccaccgagc      1800
acctcggcgg actgtccggc c                                                1821
```